(12) United States Patent
Takami et al.

(10) Patent No.: US 6,425,292 B1
(45) Date of Patent: *Jul. 30, 2002

(54) AIR DISCHARGE PRESSURE MEASURING DEVICE FOR ENDOSCOPE HAVING AN AIR SUPPLY TUBE (75) Inventors: Satoshi Takami, Saitama-ken; Junji Usami; Hidehito Kurosawa, both of Tokyo, all of (JP)

(73) Assignee: Asahi Kogaku Kogyo Kabushiki Kaisha, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/492,758

(22) Filed: Jan. 27, 2000

(30) Foreign Application Priority Data

Jan. 27, 1999 (JP) ............................. 11-018535
Jan. 27, 1999 (JP) ............................. 11-018554

(51) Int. Cl.$^7$ ................................................ G01L 9/00
(52) U.S. Cl. .................................................... 73/753
(58) Field of Search ........................... 600/118, 158, 600/160, 156, 101, 178, 560; 200/43.01; 73/714, 753, 709, 705; 361/72, 85, 802

(56) References Cited

U.S. PATENT DOCUMENTS 5,899,852 A 5/1999 Takahashi et al. ............ 600/118
6,693,649 * 2/2001 Takami et al. ................ 600/158

FOREIGN PATENT DOCUMENTS

WO 94/23644 10/1994

* cited by examiner

Primary Examiner—William Oen
(74) Attorney, Agent, or Firm—Greenblum & Bernstein, P.L.C.

(57) ABSTRACT

A discharge pressure measuring device is provided with a discharge pressure measuring system that measures a discharge pressure of the air discharged from a discharging end of an air supplying tube provided to an endoscope. The air discharged by the discharging end is directed to a pressure sensing portion of the discharging pressure measuring system through a pipe. A circuitry for obtaining a voltage representing a true discharge pressure based on a voltage output by the discharge pressure measuring member is provided. A positional relationship of the air discharge portion of the pipe with respect to the pressure sensing portion is changeable.

30 Claims, 8 Drawing Sheets

AIR DISCHARGE PRESSURE MEASURING DEVICE FOR ENDOSCOPE HAVING AN AIR SUPPLY TUBE

BACKGROUND OF THE INVENTION

The present invention relates to an air discharge pressure measuring device for measuring a discharge pressure of air that is fed by an air feeding device for an endoscope and discharged from an endoscope.

Conventionally, an air feeding device is used for feeding air into an endoscope. The air is fed by the air feeding device to, for example, a forceps channel of the endoscope. The air discharge from the endoscope is used for removing soil applied onto a cover glass of an observing optical system, for inflating human cavity so as to enable observation thereof easily, and the like.

Recently, a diagnosis method for discharging air toward a throat or a stomach and observing the condition of the portion at which the air struck has been developed. In order to apply such a diagnosis method precisely, the pressure of the air discharge from the endoscope is required to be adjusted accurately. Therefore, it is necessary to measure a discharge pressure of the air that is discharged from the endoscope and is to strike the human cavity.

SUMMARY OF THE INVENTION

It is therefore an object of the invention to provide an improved air discharging pressure measuring device for an endoscope with which the discharging pressure of the air discharged from an endoscope can be measured accurately and with stability.

For the above object, according to the present invention, there is provided a discharge pressure measuring device for an endoscope having an air supply tube to discharge the air inside a human cavity, which is provided with a discharge pressure measuring system that detects a discharge pressure of the air discharged from an outlet of the air supply tube.

Optionally, the discharge pressure measuring system may include a pressure sensor that outputs a voltage corresponding to a received pressure. In this case, the air discharge from the outlet of the air supply tube is to be directed to strike the pressure sensor.

When the pressure sensor is used, the discharge pressure measuring system can detect the discharge pressure based on the voltage output by the pressure sensor.

The outlet of the air supplying tube is fixed with respect to the endoscope so that the air is discharged to the pressure sensor under a predetermined stable condition.

Optionally, the discharge pressure measuring system may include a fixed pipe, which communicates with the air supplying tube. In this case, the air discharged from the outlet of the air supplying tube is directed, through the pipe, to a pressure sensing portion of the pressure sensor.

Further optionally, the pipe may be connected with the air supplying tube via a flexible air tube.

Further more, the air tube may connect a connectable end of the pipe and a distal end of the endoscope where the discharge port is provided to extend along a straight line.

In this case, it is preferable that the connectable end of the pipe is formed such that the air tube is not disconnected easily.

Optionally, the pressure sensing portion of the pressure sensor and the pipe are located at the same level in view of gravity, and the pressure sensing portion of the pressure sensor and a discharging end of the pipe face to each other.

In this case, it is preferable that a central axis of the pipe intersects a center of the pressure sensing portion of the pressure sensor.

Further, an area of the pressure sensing portion of the pressure sensor may be substantially equal to or greater than an area of the discharging end of the pipe.

Still optionally, the discharging pressure measuring system is constituted such that a distance between the discharging end of the pipe and the pressure sensing portion of the pressure sensor is changeable.

In this case, it is preferable that graduations are provided to the pipe for measuring the distance between the discharging end of the pipe and the pressure sensing portion of the pressure sensor is changeable.

Further optionally, the discharge pressure measuring device may be provided with a pipe supporting member. The pipe supporting member may be formed with a through hole in which the pipe is fitted, and the pipe is fixed with respect to the pipe supporting member by means of a screw.

The discharge pressure measuring device may have a body which includes a metal plate, the pipe supporting member and a lower base.

Further, a chamber for accommodating the pressure sensor may be formed by the metal plate and a sensor fixing member. The pressure sensor may be fixed to the chamber by an O-ring.

In this case, the sensor fixing member is formed to have a hole at a portion where the discharged air passes, the discharged air passed through the hole being directed to the pressure sensing portion of the pressure sensor. The hole may be sufficiently greater than the discharging end of the pipe and the pressure sensing portion of the pressure sensor.

The metal plate may be formed to have an L-shaped cross section, and the metal plate may be fixed onto the lower base such that one of two straight portion of the L-shaped cross section forms an upper surface of the body.

In this case, a circuit board mounting a circuitry for detecting the voltage representing the discharge pressure may be fixed on the metal plate by means of screws.

According to another aspect of the invention, there is provided a discharge pressure measuring device, which is provided with:

a discharge pressure measuring member that measures a discharge pressure of the air discharged from a discharging end of an air supplying tube provided to an endoscope;

a communication member that directs the air discharged by the discharging end to a pressure sensing portion of the discharging pressure measuring member;

a circuit board mounting a circuitry for obtaining a voltage representing a true discharge pressure based on a voltage output by the discharge pressure measuring member; and a casing for accommodating the discharge pressure measuring member, the communication member and the circuit board. In this case, the communication member is mounted onto the casing such that a positional relationship with respect to the pressure sensing portion is changeable.

Optionally, the communication member may include an air tube and a pipe. An end of the air tube may be connected to a distal end of the endoscope, the other end of the air tube may be connected to an end of the pipe, and the other end portion of the pipe may be mounted on the casing such that a distance to the pressure sensing portion is changeable.

Further optionally, gradations may be provided on the pipe for measuring the distance between the other end of the pipe and the pressure sensing portion.

According to a further aspect of the invention, there is provided a discharge pressure measuring device for an endoscope, which is provided with:

- a discharge pressure measuring system that measures a discharge pressure of air which is discharged from an air supplying tube provided to an endoscope with a pressure sensor;
- a peak hold processing system that holds a peak value of a voltage output by the pressure sensor, the voltage corresponding to a pressure of the discharged air;
- a reset system that resets the voltage held by the peak hold processing system;
- a short circuit preventing system that prevents short-circuiting of an electric circuitry when the voltage held by the peak hold processing system is reset.

Optionally, the peak hold circuit may include: an input operational amplifier to which the voltage output by the pressure sensor is supplied; an output operational amplifier from which a voltage is output; at least two resistors which are serially connected; a diode; a condenser; and a transistor. In this case, the short circuit preventing system should include an arrangement such that the at least two resistors being connected with the diode in parallel. The condenser is connected between a cathode of the diode and the ground, a collector of the transistor is connected with a portion where the at least two resistors are connected, and an emitter of the transistor is connected to the ground.

Optionally, the at least two resistors may include a first resistor and a second resistor, the first resistor being located on a condenser side, a resistance of the first resistor being much smaller than that of the second resistor.

Further optionally, when the voltage representing the discharge pressure is input to the input operational amplifier, the peak hold circuit accumulates electric charges in the condenser via the diode; and if the voltage input to the input operational amplifier is equal to or less than the maximum voltage, the maximum voltage is applied to the output operational amplifier.

In this case, electric charges, which corresponds to the maximum voltage, accumulated by the condenser are discharged as the input operational amplifier is connected to the ground via the first condenser and the transistor when the reset signal is transmitted to the base of the transistor.

Optionally, the voltage output by the pressure sensor may be amplified before transmitted to the peak hold circuit.

It is preferable that the amplified voltage is transmitted to an operation system, through the peak hold circuit, and directly.

In this case, the discharge pressure measuring system detects the discharge pressure based on a difference between the maximum voltage transmitted to the operation system by the peak hold circuit, and a reference voltage which is input directly to the operation system when the air is not discharged.

DESCRIPTION OF THE EMBODIMENT

Hereinafter, the present invention will be described with reference to the accompanying drawings.

Figure 1:
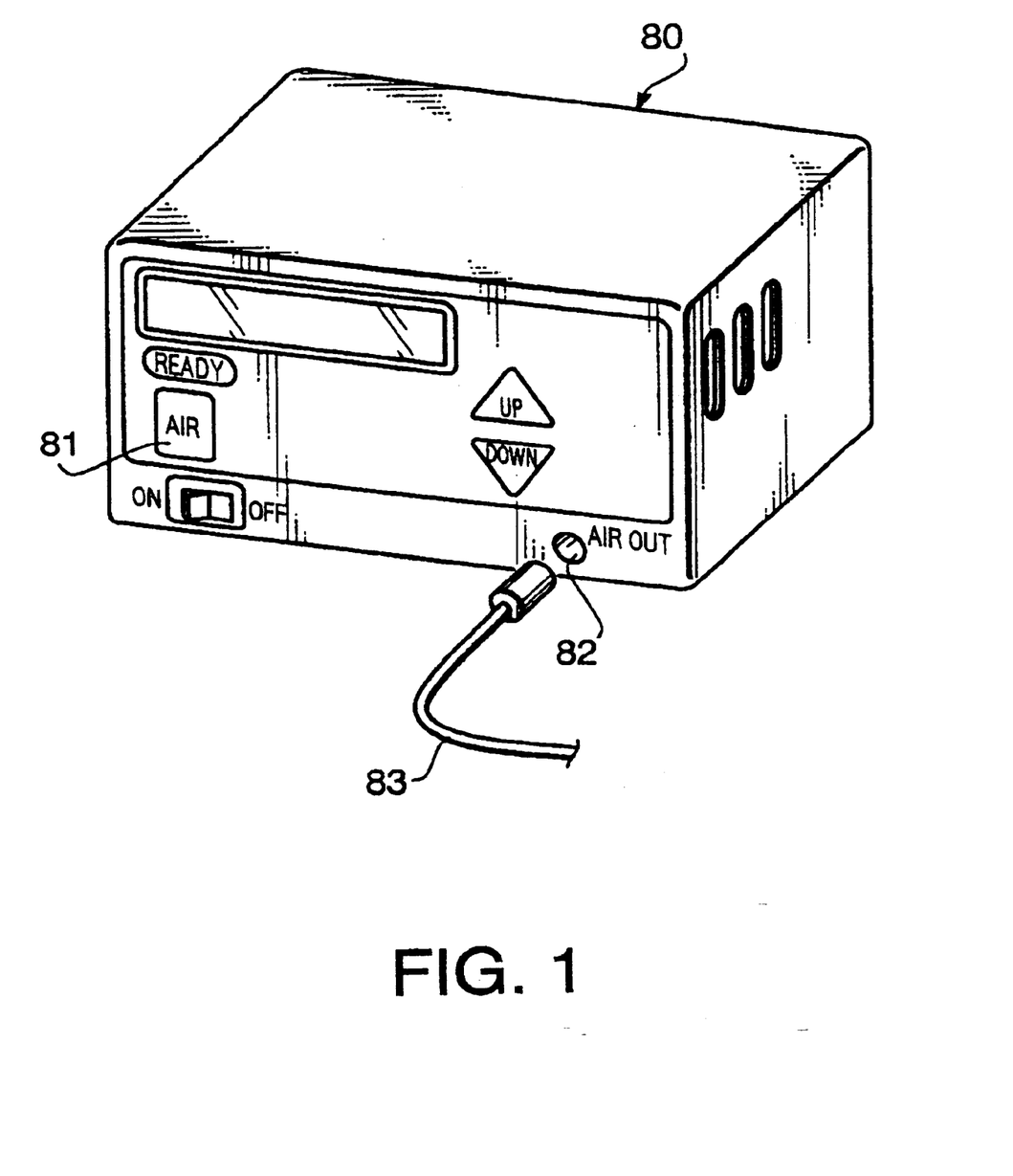
FIG. 1 is a perspective view of an air feeding device for feeding air to an endoscope.

FIG. 1 is a perspective view of an appearance of an air feeding device 80 for feeding air to an endoscope. The air is fed to, for example, in a forceps channel of the endoscope. A discharge pressure of the air fed from the air feeding device 80 and then discharged from the endoscope is measured by an air discharge pressure measuring device according to an embodiment of the present invention.

In the air feeding device 80, a sealed space for enclosing the air is provided. With use of a compressor (not shown), the pressure of the air in the sealed space is increased. By operation of a feed switch 81, a valve (not shown) provided between the sealed space and an air feeding outlet 82 is opened, and the air is fed from the outlet 82. To the outlet 82, an air tube 83 is connected, and the air fed from the outlet 82 flows through the air tube 83.

Figure 2:
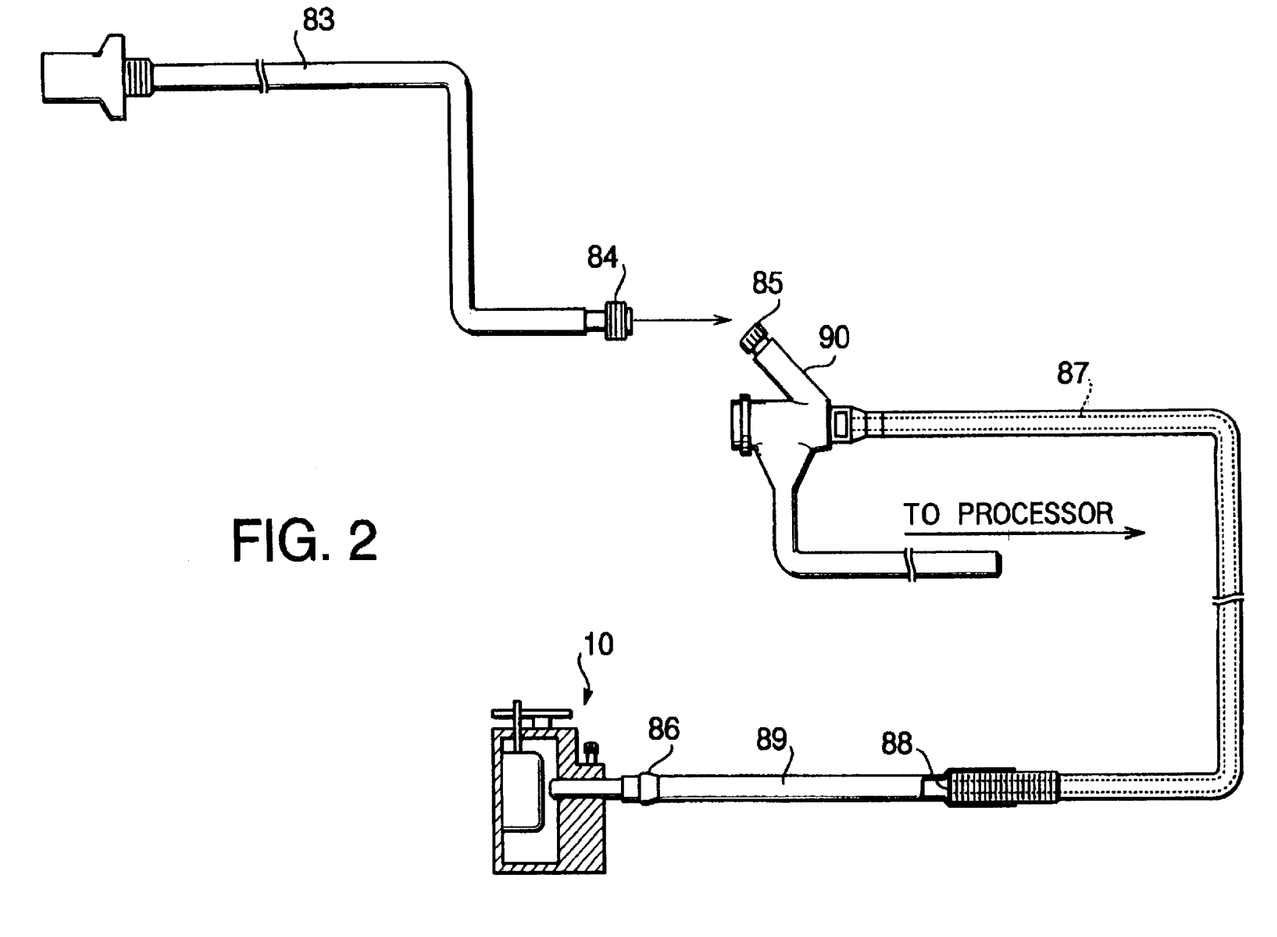
FIG. 2 shows a path of the air discharged from the air feeding device.

FIG. 2 shows a path of the air fed from the outlet 82. An end 84, which is not connected to the outlet 82, of the air tube 83 is connected to an inlet 85 of a forceps channel 87 of an endoscope 90. The endoscope 90 is to be inserted in a human body, and an image of the body cavity is captured by an image capturing element (not shown), the image signal output therefrom is processed by an image processor (not shown) and displayed on a display device (not shown).

The endoscope 90 is provided with a forceps channel 87 which is originally provided for inserting forceps for investigating living body. However, the forceps channel 87 can be used for a path of air when the air is to be delivered. The inlet 85 of the forceps channel 87 is defined at a proximal end of the forceps channel 87, and an outlet (an air discharging end) 88 is defined at a distal end of the forceps channel 87. In other words, a path for delivering the air from the outlet 82 to the outlet 88 is defined.

In the present embodiment, in order to measure a discharge pressure of the air, an air tube 89 is connected to the outlet 88. To the other end 86 of the air tube 89, a discharge pressure measuring device 10 is connected. When the air is discharged from the outlet 88 of the forceps channel 87, the discharge pressure is measured by the discharge pressure measuring device 10.

Figure 3:
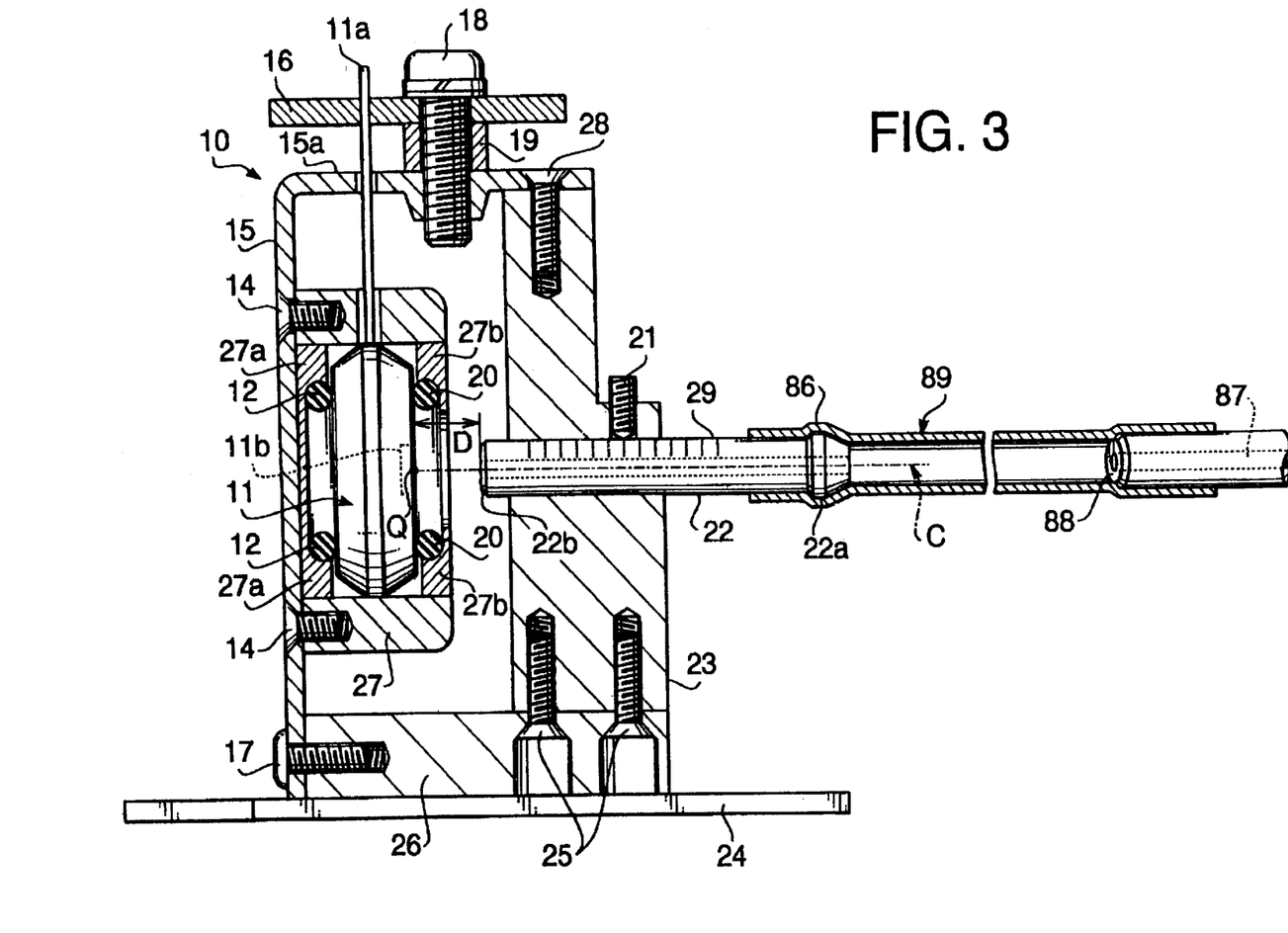
FIG. 3 is a cross sectional view of a discharge pressure measuring device according to an embodiment of the invention.

FIG. 3 is a cross sectional view of the discharge pressure measuring device 10 showing a structure thereof.

As shown in FIG. 3, inside the discharge pressure measuring device 10, a pressure sensor 11 for measuring the discharge pressure is provided. The pressure sensor 11 is formed with a receiving window 11b which receives the air directed by the air tube from the outlet 88. As an example of the pressure sensor 11, MPX5010 manufactured by Motorola may be used.

The pressure sensor 11 is accommodated in a chamber surrounded by a sensor securing member 27 and a metal plate 15. An O-ring 12 is provided between a stepped portion 27a of the securing member 27 and the pressure sensor 11. An O-ring 20 is provided between a stepped portion 27b of the securing member 27 and the pressure sensor 11. An O-ring 12 and an O-ring 20 face to each other with the pressure sensor 11 located therebetween. By the O-rings 12 and 20, the pressure sensor 11 is fixed.

The securing member 27 is fixed onto the metal plate 15 by means of fixing screws 14. On the securing member 27, a hole is formed at a position corresponding to the receiving window 11b of the pressure sensor 11. The air is directed through the hole and then received by the receiving window 11b of the pressure sensor.

The metal plate 15 has an L-shaped cross section, and to an upper portion 15a is secured to a pipe support member 23 with a screw 28. A lower base 26 and the pipe support member 23 are fixed to each other by screws 25, and a support base 24 is fixed inside the air feeding device 80 by screws (not shown). Further, the metal plate 15 is fixed on the lower base 26 with screws 17.

As described above, a body of the discharge pressure measuring device 10 is formed with the metal plate 15, the pipe support member 23, the lower base 26. The discharge pressure measuring device 10 is mounted on the supporting base 24. The upper portion 15a of the metal plate 15 and the supporting base 24 are parallel to each other, and the upper portion 15a of the metal plate 15 is maintained to extend horizontally when the discharge pressure measuring device 10 is placed for use.

A printed circuit board 16 is fixed onto the upper portion 15a of the metal plate 15 with a screw 18 with a spacer 19 located therebetween, such that the printed circuit board 16 is parallel with the supporting base 24. On the printed circuit board 16, an electrical circuit is provided for processing a voltage signal, which represents the discharge pressure, output by the pressure sensor 11, and output pins 11a of the pressure sensor 11 are soldered on the printed circuit board 16.

One end of the air tube 89 is connected to the endoscope 90, and the other end of the air tube 89 is connected to the pipe 22. The pipe is made of hard metal.

The air tube 89 is made of elastic vinyl or silicon rubber so as to prevent leakage of the air from the outlet 88 of the forceps channel. Further, a length of the air tube 89 is sufficiently short so that the air pressure is not attenuated within the air tube 89. When the discharge pressure is measured, the air tube extends straightly. Accordingly, an unstable pressure condition within the air tube due to bending of the air tube can be avoided.

An end 86 of the air tube 89, which is not connected to the endoscope 90 is connected to a connection portion 22a of the pipe 22. The shape of the connection portion 22a of the pipe 22 is formed so that the air tube 89 may not be disconnected easily. As shown in FIG. 3, the connection portion 22a is formed to be frusto-conically shaped (i.e., like a bamboo joint).

The pipe support member 23 is formed with an opening through which the pipe 22 penetrates, and the pipe 22 is fitted in the opening of the pipe support member 23. By fastening a screw 21, the pipe 22 is fixed to the pipe support member 23 with extending horizontally.

The opening formed on the pipe support member 23 is located at a position corresponding to the hole of the receiving window 11b of the pressure sensor 11. The central axis C of the pipe 22 coincides with the center Q of the receiving window 11b of the pressure sensor 11. A hole formed on the sensor fixing member 27 is sufficiently greater than the diameter of the air discharge side end 22b of the pipe 22. The air flows through the pipe 22 is directed to the receiving window 11b of the pressure sensor 11.

Figure 4:
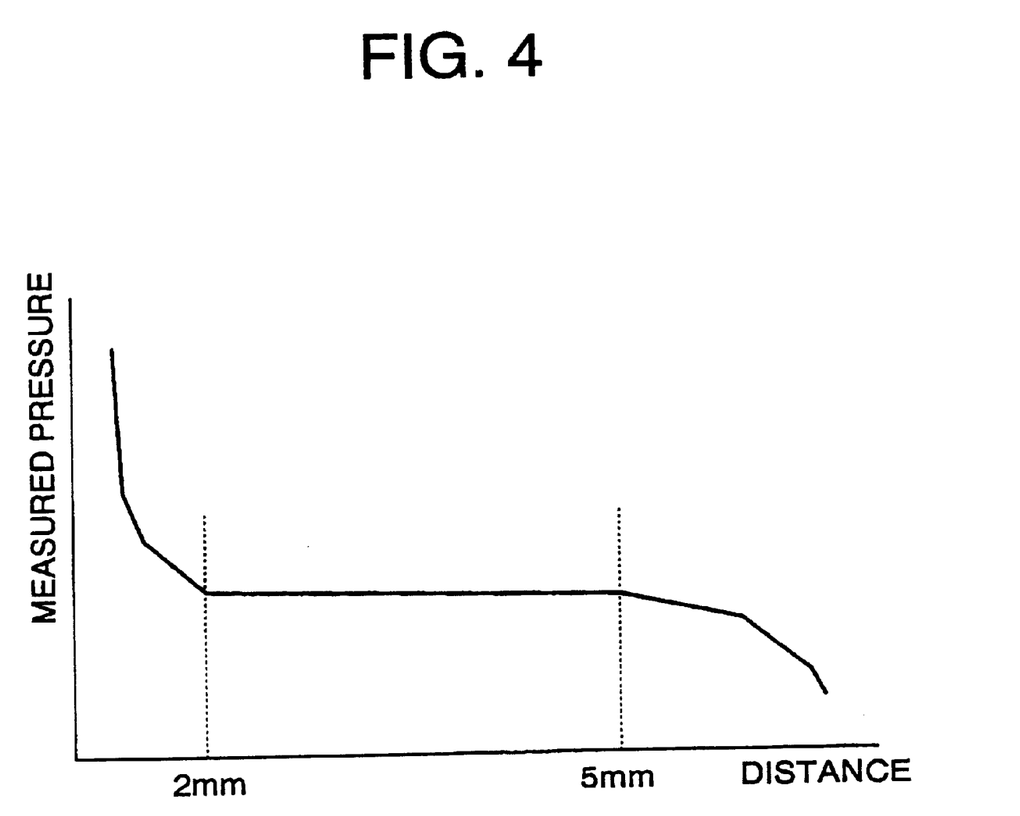
FIG. 4 is a graph showing a relationship between a measured pressure and a distance between an air discharging end of a pipe and a pressure sensing portion of a pressure sensor.

On the pipe 22, graduations 29 are formed. By loosening the screw 21, the pipe 22 can be shifted along the central axis C thereof. With the graduations 29, a distance D between the receiving window 11b and the air discharging side end 22b of the pipe 22 can be measured. Neutrally, the distance D is set to 4 mm. If the distance D is too short, a sealed condition is formed between the hole of the sensor fixing member 27 and the air discharging side end 22b, which results in a wrong measured result of the discharge pressure. If the distance D is too long, the air is released in the atmosphere before it reaches the receiving portion 11b, and in such a case, the discharge pressure may not be measured. FIG. 4 shows a graph indicating the measured discharge pressure values when the air is discharged at a predetermined pressure and the distance D is changed. As known from FIG. 4, a range of the distance D within which the air is measured in stable state is a range of 2 mm through 5 mm.

Figure 5:
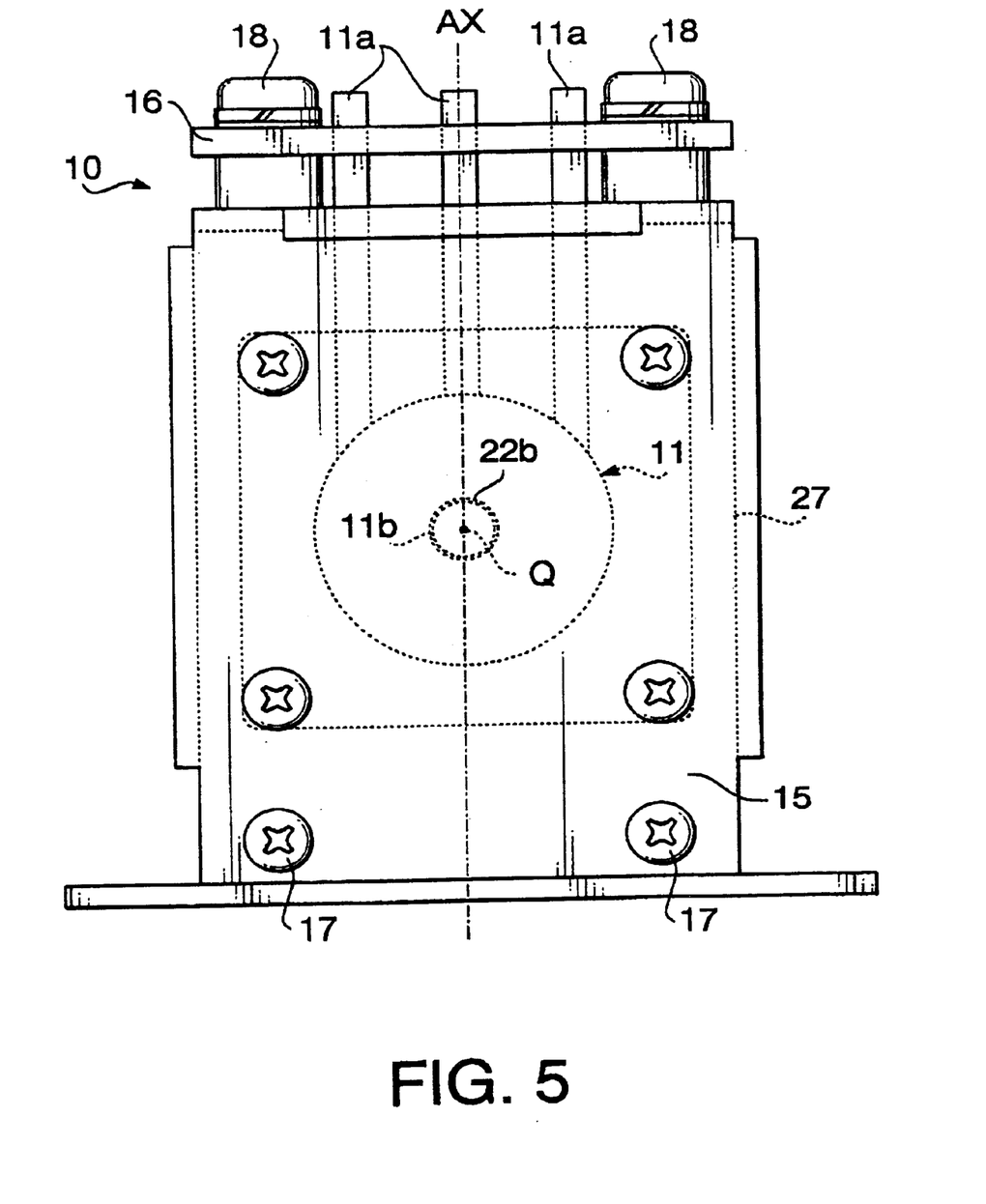
FIG. 5 is a front view of a discharge pressure measuring device according to the present invention.

FIG. 5 is a front view of the discharge pressure measuring device 10.

As shown in FIG. 5, the pressure sensor 11 is symmetrical about an axis AX. The center Q of the receiving window 11b of the pressure sensor 11 is on the central axis C (see FIG. 3) of the pipe 22. The opening of the sensor fixing member 27 and the discharging end 22b of the pipe 22 face to each other. The size of the receiving window 11b of the pressure sensor 11 and the size of the discharging end 22b of the pipe 22 is approximately the same.

Figure 6:
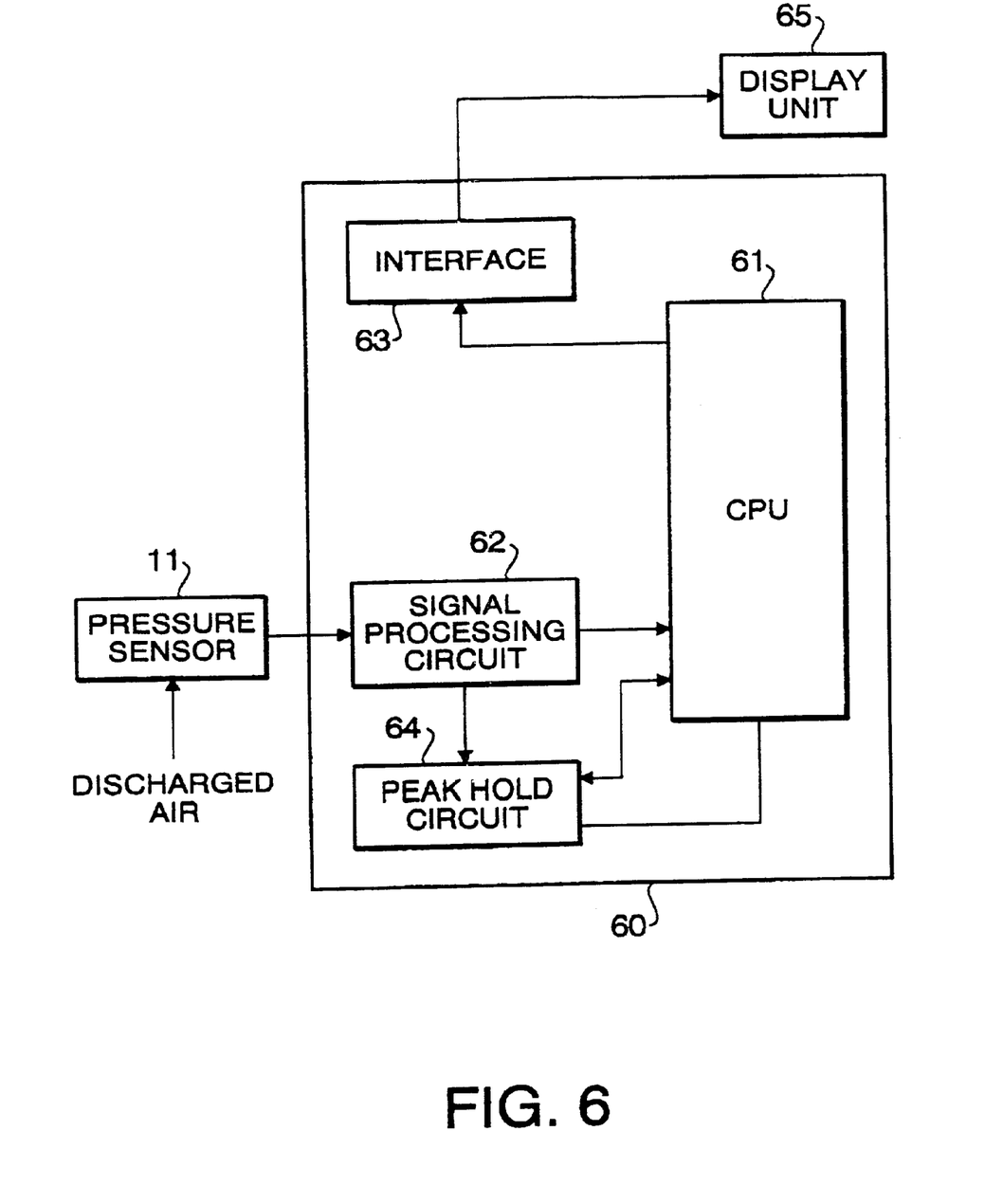
FIG. 6 is a block diagram showing a control system of the discharge pressure measuring device.

FIG. 6 is a circuit diagram illustrating an electrical circuitry provided on the printed circuit board 16 of the discharge pressure measuring device 10.

The circuitry includes a control circuit 60. In the control circuit 60, a CPU 61, a signal processing circuit 62, a signal interface 63, and a peak hold circuit 64 are provided. The pressure sensor 11 is connected to the signal processing circuit 62. The signal interface 63 is connected with an external display unit 65. The signal interface 63 converts a signal representing a measured discharge pressure output by the CPU 61 into a signal appropriate to be used for display on the display unit 65. A displayed characters (e.g., numerals) on the display unit 65 is updated every time when the discharge pressure is measured. The value of the displayed discharge pressure is stored in a memory inside the CPU 61, and the stored data is used for display until the next discharge pressure is measured.

When the air is discharged toward the receiving window 11b of the pressure sensor 11, a voltage corresponding to the pressure of the discharged air is output by the pressure sensor 11. The output voltage of the pressure sensor 11 is transmitted to the signal processing circuit 62.

The signal processing circuit 62 amplifies the received voltage. The amplified voltage value is transmitted to the peak hold circuit 64 and to the CPU 61.

The peak hold circuit 64 holds the maximum value of the voltage which changes as time elapses, and the maximum voltage is transmitted to the CPU 61.

When the discharge pressure is newly measured, a reset signal is sent from the CPU 61 to the peak hold circuit 64, and the maximum voltage held by the peak hold circuit 64 is reset. The reset signal is sent when an operator operates an externally provided switch (not shown) and/or at every predetermined period which is determined in accordance with an interval of the normal operation (i.e., measurement operations). In the latter case, the timer inside the CPU 61 is used for measuring the predetermined period, and the CPU 61 automatically outputs the reset signal every time when the predetermined period has elapsed.

The CPU 61 compares the voltage which is transmitted from the signal processing circuit 62 when the air is not discharged with the maximum voltage transmitted from the peak hold circuit 64, and an offset adjustment is performed, and the voltage corresponding to the actual discharge pressure is obtained. Specifically, the CPU 61 converts the voltage transmitted from the signal processing circuit 62 and the maximum voltage transmitted from the peak hold circuit 64 into digital data, and the calculates the difference between the voltage values, thereby obtaining the compensated voltage value corresponding to the actual discharge pressure. It should be noted that the CPU 61 ignores the voltage that is transmitted from the signal processing circuit 62 when the air is being discharged.

In order to display the measured discharge pressure as a numerical value, in accordance with the compensated voltage corresponding to the actual discharge pressure, a signal representing the discharge pressure value is transmitted, via the signal interface 63, to the display unit 65 externally provided to the discharge pressure measuring device 10.

Figure 7:
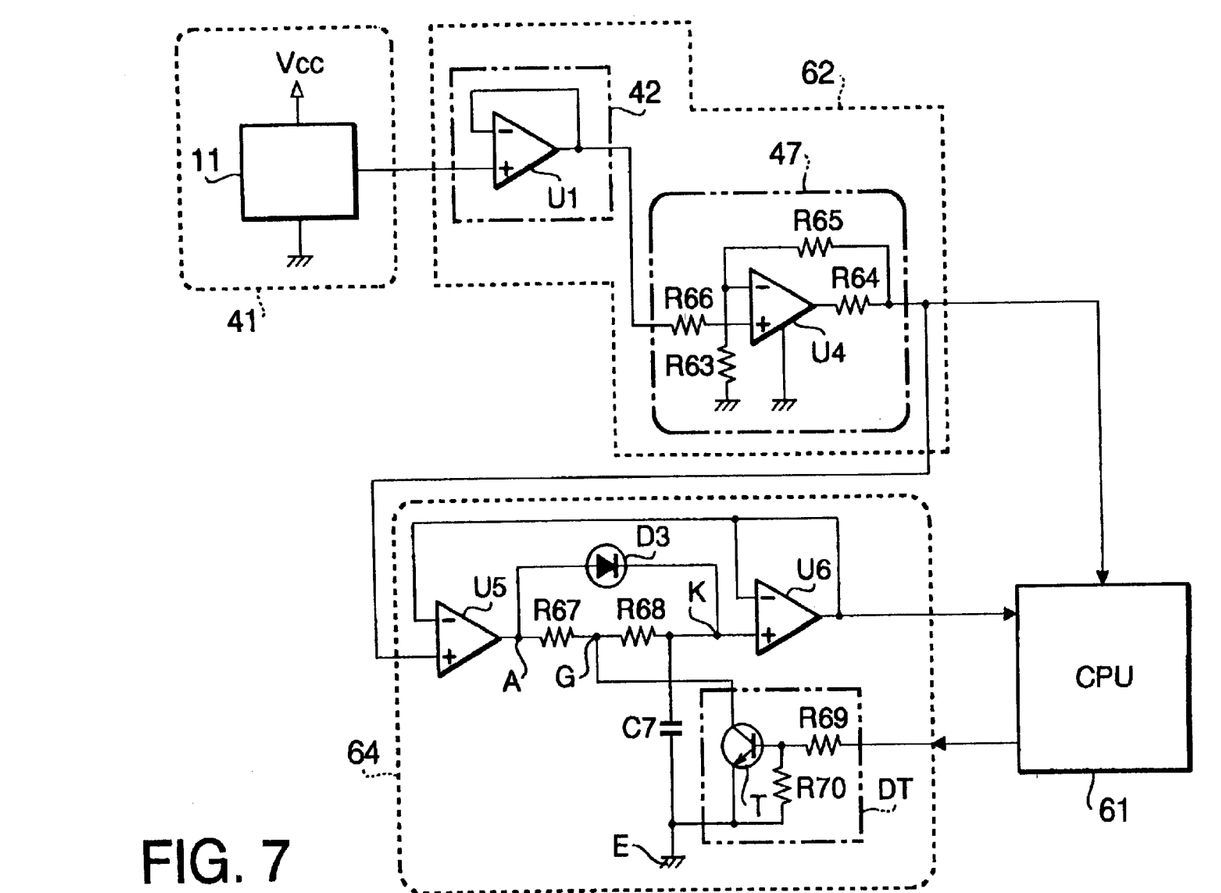
FIG. 7 is a circuit diagram of the discharge pressure measuring device.
Figure 8:
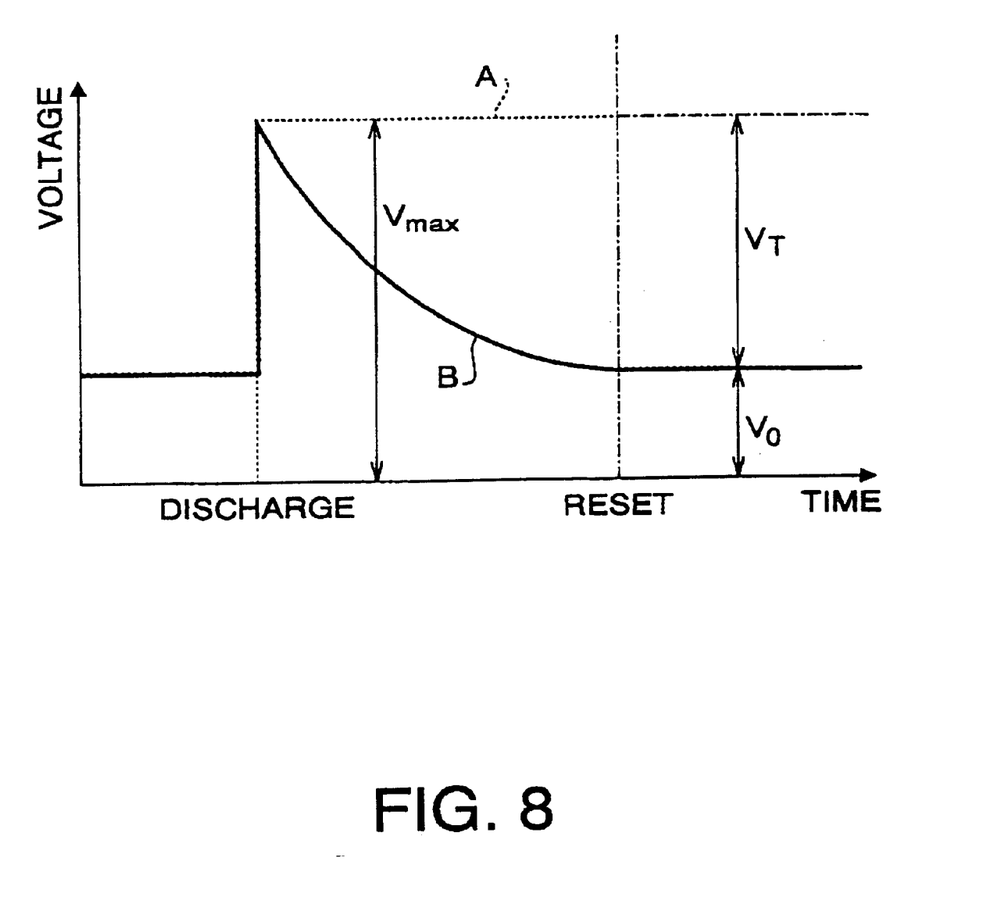
FIG. 8 is a graph showing a waveform of an output voltage of the pressure sensor.

FIG. 7 shows a circuitry provided on the printed circuit board 16 of the discharge pressure measuring device 10. FIG. 8 shows a wave form of the output voltage of the pressure sensor 11. With reference to FIGS. 7 and 8, the operation of the circuitry will be described.

The circuitry shown in FIG. 7 includes: a pressure detection circuit 41; the signal processing circuit 62 provided with a buffer circuit 42 and an amplifying circuit 47; the peak hold circuit 64; and the CPU 61.

The pressure detection circuit 41 outputs a voltage corresponding to the discharge pressure of the air that is discharged toward the pressure sensor 11. The output voltage is applied to the buffer circuit 42 which functions as an impedance converter and applies an accurate voltage value to the amplifying circuit 47.

The amplifying circuit 47 is provided with resistors R63, R64, R65 and R66, and an operational amplifier U4. The amplifying circuit 47 amplifies the voltage transmitted from the buffer circuit 42, and the amplified voltage is transmitted to both the CPU 61 and the peak hold circuit 64.

The peak hold circuit 64 is provided with operational amplifiers U5 and U6, resistors R67 and R68, a condenser C7, a diode D3, and a digital transistor DT. A digital transistor DT is provided with a transistor T and resistors R69 and R70 which function as protective resistors.

The anode of the diode D3 is connected to an output terminal of the operational amplifier U5 which is an input operational amplifier of the peak hold circuit 64, and a cathode K of the diode D3 is connected to an non-inverting input terminal of the operational amplifier U6. Resistors R67 and R68 which are connected in series are provided between the output terminal of the operational amplifier U5 and the non-inverting input terminal of the operational amplifier U6, in parallel with the diode D3. The output terminal of the operational amplifier U6 is connected to the CPU 61, and to the inverting input terminals of the operational amplifiers U5 and U6.

An end C7 of the condenser C7 is connected with the cathode of the diode D3 and with the non-inverting input terminal of the operational amplifier U6. The other end of the condenser C7 is grounded (i.e., connected to the ground E).

A collector of the digital transistor DT is connected to a point G where the resistors R67 and R68 are connected. An emitter of the digital transistor DT is connected to the ground E. A base of the digital transistor DT is connected to the CPU 61 via the resistor R69, and to the ground E via the resistor R70. The resistance of the resistor R67 is much greater than that of the resistor R68.

The amplified voltage output by the amplifying circuit 47 is input to the operational amplifier U5, and then transmitted to the operational amplifier U6 via the diode D3. The electric charge is accumulated in the condenser C7 in accordance with the voltage input to the operational amplifier U5.

Since the air is discharged momentarily, the voltage input to the operational amplifier U5 varies as time elapses, and therefore the waveform has a shape indicated by a solid line B in FIG. 8. As shown in FIG. 8, the peak of the voltage appears at the beginning of the waveform.

When the voltage input to the operational amplifier U5 is greater than the voltage across the condenser C7, the input voltage is applied to the operational amplifier U6 through the diode D3, and then transmitted to the CPU 61. When the voltage input to the operational amplifier U5 is smaller than the voltage across the condenser C7, due to the characteristic of the diode D3, the voltage applied to the operational amplifier U5 is not transmitted to the CPU 61, and the voltage across the condenser C7 is applied to the operational amplifier U6 instead. With this configuration, the maximum voltage (which is indicated by broken lines A in FIG. 8) of the voltage corresponding to the discharge pressure, which changes as time elapses, is always transmitted to the CPU 61. Thus, the peak value of the voltage applied to the operational amplifier U5 is held.

A reset signal is to be input, from the CPU 61, to the base of the transistor T through the resistor R69. When the reset signal is input to the digital transistor, the digital transistor DT is set to an ON condition, and the electric charge accumulated in the condenser C7 is discharged. At this stage, the operational amplifier U5 is connected to the ground E via the diode D3, the resistor R68 and the digital transistor DT, and the electric charge accumulated in the condenser C7 is discharged through the resistor R68 and the digital transistor DT.

The operational amplifier U5 is not directly connected to the ground E when the reset signal is output by the CPU 61. That is, when the reset signal is output by the CPU 61, the operational amplifier U5 is connected to the ground E through the resistor R68, and accordingly, the operational amplifier U5 is not overloaded. In this embodiment, as described above, the reset signal is output when the operator operates a predetermined switch when (i.e., immediately before) the discharge pressure is measured.

Since the condenser C7 is connected to the ground E of the operational amplifier U5 through the resistors R67 and R68, the electric charge accumulated therein is discharged as the time elapses. Since the resistance of the serially connected resistors R67 and R68 is relatively large, even if the reset signal is not transmitted, the electric charge accumulated in the condenser C7 is discharged within a relatively long period which is much greater than an interval between discharge of the air and the output of the reset signal (i.e., a period during which the peak hold operation is executed).

The resistance of the resistor R68 is very small in comparison with the resistor R67. Accordingly, when the reset signal is output by the CPU 61, the electric charge of the condenser C7 is immediately discharged, and a succeeding measurement can be executed immediately. In the embodiment, the resistance of the resistor R67 is about 500 kΩ, and the resistance of the resistor R68 is about 1 kΩ.

The maximum voltage Vmax applied, by the peak hold circuit 64, to the CPU 61, and a reference voltage Vo which is a voltage applied by the signal processing circuit 62 to the CPU 61 when the air is not being discharged are converted to digital data, compared by the CPU 61, and a difference (i.e., the compensated) voltage Vt representing the true discharge pressure is obtained (see FIG. 8). That is, an offset adjustment is performed for removing the voltage Vo, which is detected when the air is not discharged, from the voltage Vmax which is considered to be a sum of the voltage Vo and a voltage corresponding to the true discharge pressure.

As described above, according to the above-described embodiment, by connecting the endoscope 90 to the pipe 20 via the air tube, and directing the air discharged from the discharging end 22b of the pipe 22 to the receiving window 11b of the pressure sensor 11, the discharge pressure which is to be discharged into the human cavity from the outlet of the forceps channel 90 can be measured.

Generally, it is difficult to measure the discharge pressure since a positional relationship from the outlet 22b of the pipe 22 to the receiving window 11b of the pressure sensor 11 is unstable. However, according to the above-described embodiment, since the rigid pipe 22 is inserted in a pipe supporting member 27 and fixed by a screw 21, the measurement can be done under a stable condition. Further, in the embodiment, the pipe 22 and the receiving window 11b of the pressure sensor 11 is located at the same height so that the air enters the receiving window 11b correctly, and the pipe 11 and the pressure sensor 11 are arranged such that the outlet 22b of the pipe 22 faces the receiving window 11b of the pressure sensor 11, the air is discharged under an optimum condition, and the discharge pressure can be measured accurately.

According to the above-described embodiment, a distance D between the outlet 22b of the pipe 22 and the receiving window 11b of the pressure sensor 11 can be changed. Therefore, an appropriate position at which the discharge pressure can be measured under the most stable condition can be set, and the discharge pressure can be measured accurately. Further, if the pressure sensor is exchanged to another, the distance D can be changed to a distance appropriate to the exchanged pressure sensor 11.

In the above-described embodiment, the air tube 89 is formed as short as possible. Therefore, the pressure will not be wasted and attenuated. Further, the connection portion 22a is formed to be a frusto-conically-shaped (i.e., shaped like a bamboo joint), and therefore, leakage of the air can be avoided.

In the peak hold circuit 64, the diode D3 and serially connected resistors R67 and R68 are provided, in parallel, between the operational amplifiers U5 and U6. With this configuration, when the reset signal is output by the CPU 61, the output terminal of the operational amplifier U5 is not short-circuited, and accordingly, the unstable performance of the circuit is avoided. Therefore, the reset signal can be sent to the peak hold circuit 64 at a timing when there are less noises, and the waveform of the measured voltage representing the discharge pressure is stabilized.

Since the resistance of the serially connected resistors R67 and R68 is relatively large, the electric charge accumulated in the condenser C7 is naturally discharged within a relatively long period of time. Even if the reset signal is not output by the CPU 61, the electric charge is discharged in due time, and therefore, in the succeeding measurement, even if the measured voltage is lower than the previously measured value, the discharge pressure can be measured correctly.

The output signal of the signal processing circuit 62 and the peak hold circuit 64 is applied to the CPU 61, the CPU 61 can apply the offset adjustment, and the voltage Vt representing the true discharge pressure can be obtained. Further, the voltage representing the discharge voltage can be obtained without being affected by a drift which occurs as time elapses.

The resistance of each of the resistors R67 and R68 can be changed arbitrarily under a condition that the resistance of the resistor R67 is much greater than that of the resistor R68.

Optionally, the display unit may be constituted to display a plurality of areas each for displaying a discharge value. With such a configuration, the previous discharge value and the current discharge value may be displayed so that the operator can compare the values.

Further optionally, the display unit 65 may be provided on the metal plate 15 of the discharge pressure measuring device 10.

Generally, the discharge pressure P when the air is discharged toward a flat plate can be obtained by the following formula (1).

$$P = \rho \times F \times V \times \sin\alpha \tag{1}$$

where, ρ represents a density of the fluid (i.e., the air), F represents the flowing amount per a unit interval, V represents a speed of the fluid, and α represents an angle at which the fluid strikes the flat plate (in the above embodiments, α=90 degrees).

Each term of the formula (1) may be multiplied by a coefficient depending on a condition, i.e., the shape of the flat plate, a distance between the discharged point to the flat plate, and the like. Thus, in order to measure the discharge pressure, the condition should be adjusted appropriately in accordance with the individual discharge pressure measuring device.

As described above, according to the present invention, the discharge pressure can be measured under a stable condition. Further, even if a reset operation is performed for the maximum voltage obtained by the peak hold circuit, the performance of the electric circuitry may not become unstable, and the discharge pressure can always be obtained under a stable condition.

The present disclosure relates to the subject matters contained in Japanese Patent Applications No. HEI 11-018535 and No. HEI 11-018554, both filed on Jan. 27, 1999, which are expressly incorporated herein by reference in their entireties.

What is claimed is:

1. A discharge pressure measuring device for an endoscope having an air supply tube to discharge the air inside a human cavity, comprising:
    a discharge pressure measuring system that detects a discharge pressure of the air discharged from an outlet of the air supply tube.

2. The discharge pressure measuring device according to claim 1, wherein said discharge pressure measuring system includes a pressure sensor that outputs a voltage corresponding to a received pressure, said air discharged from the outlet of the air supply tube being directed to strike said pressure sensor.

3. The discharge pressure measuring device according to claim 2, wherein said discharge pressure measuring system detects the discharge pressure based on the voltage output by said pressure sensor.

4. The discharge pressure measuring device according to claim 3, wherein the outlet of said air supply tube is fixed with respect to the endoscope so that the air is discharged to said pressure sensor under a predetermined stable condition.

5. The discharge pressure measuring device according to claim 4, wherein said discharge pressure measuring system includes a fixed pipe, said pipe communicating with the air supply tube, the air discharged from the outlet of the air supply tube being directed, through said pipe, to a pressure sensing portion of said pressure sensor.

6. The discharge pressure measuring device according to claim 5, wherein said pipe is connected with the air supply tube via a flexible air tube.

7. The discharge pressure measuring device according to claim 6, wherein said air tube connects a connectable end of said pipe and a distal end of the endoscope where the discharge port is provided to extend along a straight line.

8. The discharge pressure measuring device according to claim 7, wherein the connectable end of said pipe is formed such that the air tube is not disconnected easily.

9. The discharge pressure measuring device according to claim 5, wherein the pressure sensing portion of said pressure sensor and said pipe are located at a same level in view of gravity, and wherein the pressure sensing portion of said pressure sensor and a discharging end of said pipe face each other.

10. The discharge pressure measuring device according to claim 9, wherein a central axis of said pipe intersects a center of the pressure sensing portion of said pressure sensor.

11. The discharge pressure measuring device according to claim 9, wherein an area of said pressure sensing portion of said pressure sensor is substantially equal to or greater than an area of the discharging end of said pipe.

12. The discharge pressure measuring device according to claim 5, wherein said discharging pressure measuring system is constituted such that a distance between the discharging end of said pipe and the pressure sensing portion of said pressure sensor is changeable.

13. The discharge pressure measuring device according to claim 12, wherein graduations are provided to said pipe for measuring the distance between the discharging end of said pipe and the pressure sensing portion of said pressure sensor.

14. The discharge pressure measuring device according to claim 12, further comprising a pipe supporting member, said pipe supporting member being formed with a through hole in which said pipe is fitted, said pipe being fixed with respect to said pipe supporting member by fastening a screw.

15. The discharge pressure measuring device according to claim 14, a body of which including a metal plate, said pipe supporting member and a lower base.

16. The discharge pressure measuring device according to claim 15, wherein a chamber for accommodating said pressure sensor is formed by said metal plate and a sensor fixing member, said pressure sensor being fixed to said chamber by an O-ring.

17. The discharge pressure measuring device according to claim 16, wherein said sensor fixing member is formed to have a hole at a portion where the discharged air passes, the discharged air passed through said hole being directed to said pressure sensing portion of said pressure sensor, said hole being sufficiently greater than the discharging end of said pipe and said pressure sensing portion of said pressure sensor.

18. The discharge pressure measuring device according to claim 15, wherein said metal plate is formed to have an L-shaped cross section, said metal plate being fixed onto said lower base such that one of two straight portion of said L-shaped cross section forms an upper surface of said body.

19. The discharge pressure measuring device according to claim 18, wherein a circuit board mounting a circuitry for detecting the voltage representing the discharge pressure is fixed on said metal plate by means of screws.

20. A discharge pressure measuring device, comprising:
   a discharge pressure measuring member that measures a discharge pressure of the air discharged from a discharging end of an air supplying tube provided to an endoscope;
   a communication member that directs the air discharged by said discharging end to a pressure sensing portion of said discharging pressure measuring member;
   a circuit board mounting a circuitry for obtaining a voltage representing a true discharge pressure based on a voltage output by said discharge pressure measuring member; and
   a casing for accommodating said discharge pressure measuring member, said communication member and said circuit board, and
   wherein said communication member is mounted to said casing such that a positional relationship with respect to said pressure sensing portion is changeable.

21. The discharge pressure measuring device according to claim 20, wherein said communication member includes an air tube and a pipe, an end of said air tube being connected to a distal end of said endoscope, the other end of said air tube being connected to an end of said pipe, the other end portion of said pipe being mounted on said casing such that a distance to said pressure sensing portion is changeable.

22. The discharge pressure measuring device according to claim 21, wherein graduations are provided on said pipe for measuring the distance between said the other end of said pipe and said pressure sensing portion.

23. An discharge pressure measuring device for an endoscope, comprising:
   a discharge pressure measuring system that measures a discharge pressure of air which is discharged from an air supplying tube provided to an endoscope with a pressure sensor;
   a peak hold processing system that holds a peak value of a voltage output by said pressure sensor, said voltage corresponding to a pressure of the discharged air;
   a reset system that resets the voltage held by said peak hold processing system;
   a short circuit preventing system that prevents short-circuiting of an electric circuitry when the voltage held by said peak hold processing system is reset.

24. The discharge pressure measuring device according to claim 23, wherein said peak hold circuit includes:
   an input operational amplifier to which the voltage output by said pressure sensor;
   an output operational amplifier from which a voltage is output;
   at least two resistors which are serially connected;
   a diode;
   a condenser; and
   a transistor,
   wherein said short circuit preventing system includes an arrangement such that said at least two resistors being connected with said diode in parallel, said condenser being connected between a cathode of said diode and the ground, a collector of said transistor being connected with a portion where said at least two resistors are connected, an emitter of said transistor being connected to the ground.

25. The discharge pressure measuring device according to claim 24, wherein said at least two resistors include a first resistor and a second resistor, said first resistor being located on a condenser side, a resistance of said first resistor being much smaller than that of said second resistor.

26. The discharge pressure measuring device according to claim 24, wherein, when the voltage representing the discharge pressure is input to said input operational amplifier, said peak hold circuit accumulates electric charges in said condenser via said diode; and wherein if the voltage input to said input operational amplifier is equal to or less than said peak value of a voltage, the peak value of a voltage is applied to said output operational amplifier.

27. The discharge pressure measuring device according to claim 24, wherein said reset system transmits a reset signal to a base of said transistor, electric charges, which corresponds to the peak value of a voltage, accumulated by said condenser being discharged as said input operational amplifier is connected to the ground via said first resistor and said transistor when the reset signal is transmitted to the base of said transistor.

28. The discharge pressure measuring device according to claim 24, wherein the voltage output by said pressure sensor is amplified before transmitted to said peak hold circuit.

29. The discharge pressure measuring device according to claim 28, wherein the amplified voltage is transmitted to an operation system, through said peak hold circuit, and directly.

30. The discharge pressure measuring device according to claim 29, wherein said discharge pressure measuring system detects the discharge pressure based on a difference between the peak value of a voltage transmitted to the operation system by said peak hold circuit, and a reference voltage which is input directly to the operation system when the air is not discharged.

* * * * *